(12) United States Patent
Bazemore et al.

(10) Patent No.: US 11,850,037 B2
(45) Date of Patent: *Dec. 26, 2023

(54) APPARATUSES AND METHODS FOR EXTRACTING CHEMICALS FROM BODILY CAVITIES AND BREATH

(71) Applicant: Volatile Analysis Corporation, Grant, AL (US)

(72) Inventors: Russell Bazemore, Grant, AL (US); Kathy Bazemore, Grant, AL (US)

(73) Assignee: Volatile Analysis Corporation, Grant, AL (US)

( * ) Notice: Subject to any disclaimer, the term of this patent is extended or adjusted under 35 U.S.C. 154(b) by 408 days.

This patent is subject to a terminal disclaimer.

(21) Appl. No.: 16/900,212

(22) Filed: Jun. 12, 2020

(65) Prior Publication Data
US 2021/0100479 A1 Apr. 8, 2021

Related U.S. Application Data

(63) Continuation of application No. 15/280,395, filed on Sep. 29, 2016, now Pat. No. 10,709,356, which is a
(Continued)

(51) Int. Cl.
*A61B 5/097* (2006.01)
*G01N 1/40* (2006.01)
(Continued)

(52) U.S. Cl.
CPC .............. *A61B 5/097* (2013.01); *A61B 5/082* (2013.01); *A61B 10/0051* (2013.01); *A61C 5/90* (2017.02);
(Continued)

(58) Field of Classification Search
None
See application file for complete search history.

(56) References Cited

U.S. PATENT DOCUMENTS 3,886,949 A * 6/1975 Hurst .................... A61J 17/105
606/236
7,387,899 B1 6/2008 D'Angelo
(Continued)

FOREIGN PATENT DOCUMENTS

WO 9720502 A1 6/1997
WO WO-9720502 A1 * 6/1997 ......... A61B 10/0051

OTHER PUBLICATIONS

Machine Translation of WO 97/20502 (Year: 1997).*
(Continued)

*Primary Examiner* — Michael R Bloch
(74) *Attorney, Agent, or Firm* — Butler Snow LLP; Jon E. Holland

(57) ABSTRACT

A chemical extraction apparatus has absorbent material for absorbing or adsorbing volatile chemicals from a breath of a user. The chemical extraction apparatus is positioned within such that breaths from the user flow over the absorbent material thereby causing volatile chemicals in the breaths to absorb or adsorb into the absorbent material. The absorbent material is then analyzed to determine the amount of chemicals absorbed or adsorbed into the absorbent material. Based on such analysis, various diseases or conditions can be detected or diagnosed.

5 Claims, 22 Drawing Sheets

Related U.S. Application Data continuation of application No. 12/772,016, filed on Apr. 30, 2010, now Pat. No. 9,480,461, which is a continuation-in-part of application No. 12/401,051, filed on Mar. 10, 2009, now abandoned.

(60) Provisional application No. 61/174,327, filed on Apr. 30, 2009, provisional application No. 61/148,297, filed on Jan. 29, 2009, provisional application No. 61/036,646, filed on Mar. 14, 2008, provisional application No. 61/036,673, filed on Mar. 14, 2008, provisional application No. 61/035,266, filed on Mar. 10, 2008.

(51) Int. Cl.
  *A61J 17/00* (2006.01)
  *A61C 5/90* (2017.01)
  *A61B 10/00* (2006.01)
  *A61B 5/08* (2006.01)
  *G01N 1/22* (2006.01)
  *A61J 7/00* (2006.01)

(52) U.S. Cl.
  CPC .............. *A61J 17/001* (2015.05); *G01N 1/22* (2013.01); *G01N 1/405* (2013.01); *A61B 2010/0087* (2013.01); *A61J 7/0092* (2013.01); *G01N 1/4044* (2013.01); *G01N 2001/2244* (2013.01)

(56) References Cited

U.S. PATENT DOCUMENTS

| | | | |
|---|---|---|---|
| 2003/0034031 A1* | 2/2003 | Lev | A61J 17/001 128/200.24 |
| 2003/0106555 A1* | 6/2003 | Tovey | A61F 5/08 128/205.27 |
| 2005/0065446 A1 | 3/2005 | Talton | |
| 2010/0004555 A1 | 1/2010 | Bazemore et al. | |
| 2010/0312133 A1 | 12/2010 | Bazemore et al. | |

OTHER PUBLICATIONS

Machine Translation of WO9720502A1.
Bazemore, et al., U.S. Appl. No. 15/280,395, entitled, "Apparatuses and Methods for Extracting Chemicals From Bodily Cavities and Breath," filed Sep. 29, 2016.

* cited by examiner

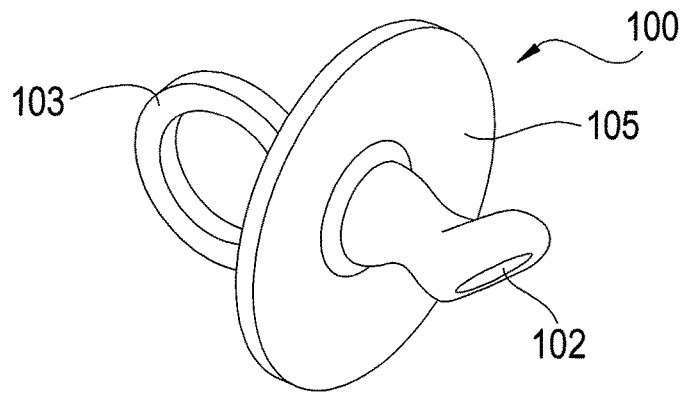
FIG. 14
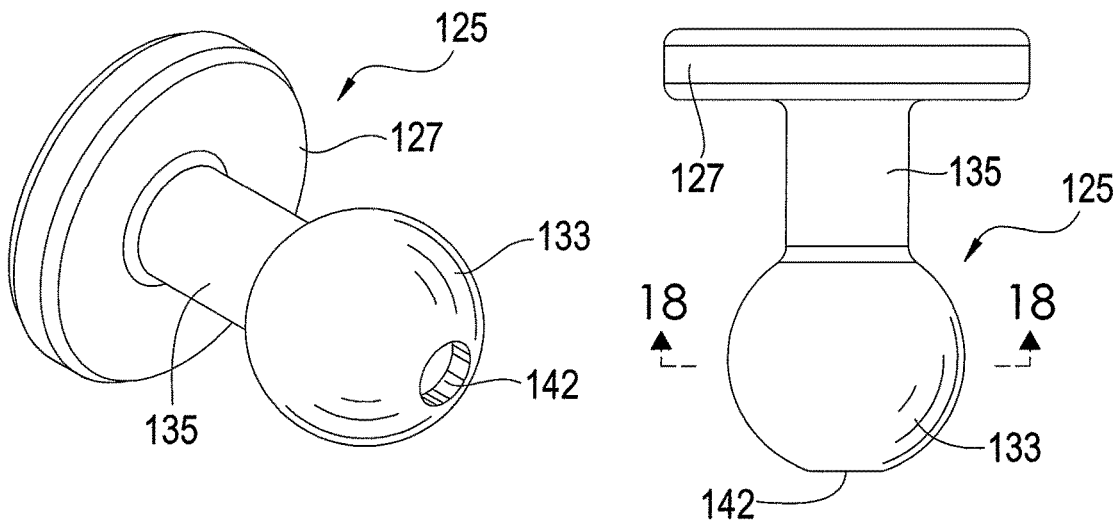
FIG. 15
FIG. 16
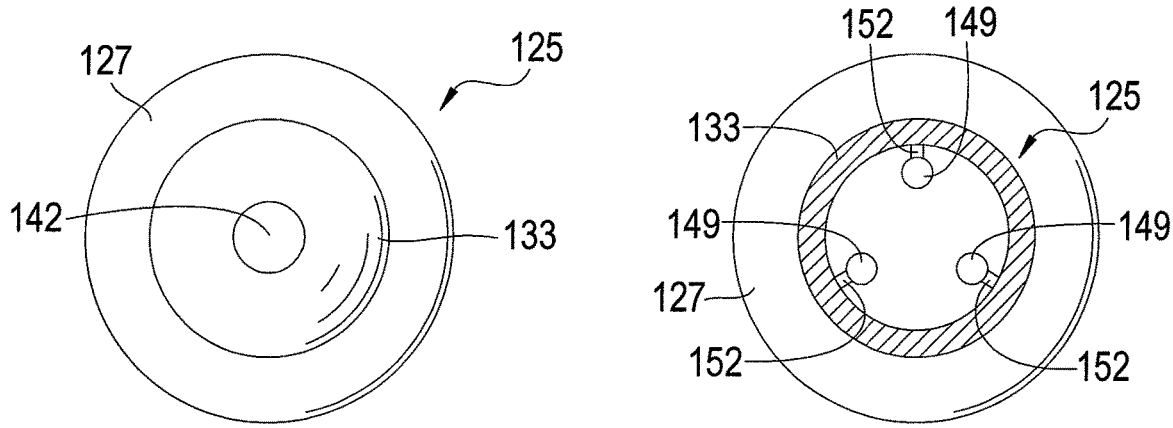
FIG. 17
FIG. 18

(End View)

(Side View)

(End View)

(Side View)

(End View)

(End View)

(End View)

APPARATUSES AND METHODS FOR EXTRACTING CHEMICALS FROM BODILY CAVITIES AND BREATH

CROSS REFERENCE TO RELATED APPLICATIONS

This application is a continuation of and claims priority to U.S. patent application Ser. No. 15/280,395, entitled "Apparatuses and Methods for Extracting Chemicals from Bodily Cavities and Breath," and filed on Sep. 29, 2016. U.S. patent application Ser. No. 15/280,395 is a continuation of and claims priority to U.S. patent application Ser. No. 12/772,016, entitled "Methods for Extracting Chemicals from Nasal Cavities and Breath," and filed on Apr. 30, 2010. U.S. patent application Ser. No. 12/772,016 claims priority to U.S. patent application Ser. No. 12/401,051, entitled "Apparatuses and Methods for Extracting Chemicals from the Oral Cavity and Breath," and filed on Mar. 10, 2009, which is incorporated herein by reference. U.S. patent application Ser. No. 12/772,016 claims priority to U.S. Provisional Patent Application No. 61/174,327, entitled "Apparatuses and Methods for Extracting Chemicals from the Oral Cavity and Breath," and filed on Apr. 30, 2009, which is incorporated herein by reference. U.S. patent application Ser. No. 12/401,051 claims priority to U.S. Provisional Patent Application No. 61/035,266, entitled "Method and Apparatus for Extracting Volatile and Semi-Volatile Compounds from the Oral Cavity and Breath," and filed on Mar. 10, 2008, which is incorporated herein by reference. U.S. patent application Ser. No. 12/401,051 also claims priority to U.S. Provisional Patent Application No. 61/036,673, entitled "Chewing Device for Extracting Volatile and Semi-Volatile Compounds from the Oral Cavity and Breath, and Method for Making Same," and filed on Mar. 14, 2008, which is incorporated herein by reference. U.S. patent application Ser. No. 12/401,051 claims priority to U.S. Provisional Patent Application No. 61/036,646, entitled "Method and Apparatus for Extracting Volatile, Semi-Volatile Compounds from the Oral Cavity and Breath," and filed on Mar. 14, 2008, which is incorporated herein by reference. U.S. patent application Ser. No. 12/401,051 claims priority to U.S. Provisional Patent Application No. 61/148,297, entitled "Apparatuses and Methods for Extracting Chemicals from the Oral Cavity and Breath," and filed on Jan. 29, 2009, which is incorporated herein by reference.

RELATED ART

Advances in instrumentation have resulted in new generations of reliable, accurate, and precise tools for the scientist (analytical chemist, food scientist, biochemist, biologist). Technical advances have opened new areas for research including the field of metabolomics, the study of metabolites produced in the body related to disease. Metabolomics is a rapidly growing research field and promises to make disease detection and diagnosis less invasive and much more rapid. Difficult and time consuming procedures that currently require blood, stool, urine, or even more invasive tissue collection samples will be required much less frequently, or not at all. Sources of metabolites include blood, urine, feces, sweat, and breath. Breath analysis is challenging because compounds present are smaller (lower molecular weight, typically less than 300 g/mole), volatile (exist preferentially in the gas state), and reactive. Trace levels of metabolites in breath add another dimension of difficulty because of the quantity of breath needed to pull out sufficient mass of compound to permit detection is relatively large.

Current methods for breath collection for subsequent analysis include exhaling one or two breaths directly into an instrument, or collecting from 2 or 3 breaths to many (0.6 to 250 L) into a Tedlar bag—an air-tight bag made of Teflon, plastic, or other inert material. Problems with these methods, however, limit their usefulness. For example, very low levels, e.g., less than 1 part per trillion, of metabolites present in the amount of breath analyzed are not typically sufficient to detect, or are detected with difficulty, by the most sensitive instrumentation. Also, methods for breathing directly into an instrument are cumbersome, inconvenient, and require that the user and instrument be present in the same location.

For example researchers at Menssana Research have developed Breathscanner 2.5, an instrument that incorporates gas chromatography and a detector to identify volatiles from the breath of users (e.g., patients) who breathe directly into an interface with the instrument. This device is cumbersome, and results are dependent upon the amount of a substance present in breath collected in the short time a user exhales into the device. U.S. Pat. No. 5,465,728 describes a hand held device measuring breath components. While portable, this device appears to lack trace level detection capability. Other methods for measuring breath include US Patent Pub. No. 2008/0008666 A1, which describes a method for monitoring the effectiveness of oral malodor treatment by measuring for specific chemicals listed. It does not appear to allow for novel extraction and detection means. Finally, a major flaw associated with collecting large quantities of breath with a Tedlar bag is the problem of transferring the metabolite present in a large volume of air into an instrument while eliminating the dilution effect. This method provides no means for concentrating metabolites. Also with bags, some volatile metabolites are absorbed into the bag construction materials, or stick (adsorb) to the sides thus unavailable for detection and measurement.

Accordingly, a device is needed to extract low levels (trace levels) of volatile, semi-volatile, and non-volatile compounds from breath, for the purpose of advancing the field of breath metabolomics. Such a device would also be useful in dental, food and flavor sciences. For example, in dental science, oral health may be assessed by sampling metabolites present in the saliva and breath. Common maladies such as gum health may be diagnosed based on the presence and concentration of known metabolites generated by infection including compounds associated with foul odor such as carbon disulfide, methyl mercaptan, and dimethyl sulfide. In food and flavor sciences, flavor and taste are known as chemosenses, meaning the sense of taste and smell (flavors, tastes and fragrances) are the brain's interpretation of signals generated by interactions of chemicals (from foods and fragrances) with receptors in the mouth and nose. By detecting and measuring these chemicals in the oral cavity, improvements in flavor and fragrance technologies, duration, and efficacy may be successfully measured at a level currently unavailable. For example how long a product freshens your breath, or how long a product provides a pleasant taste may be more accurately assessed by measuring the time a breath freshening chemical resides in the oral cavity before being rinsed away in saliva or exhaled in air.

BRIEF DESCRIPTION OF THE DRAWINGS

The disclosure can be better understood with reference to the following drawings. The elements of the drawings are

FIG. 14 illustrates a chemical extraction apparatus in accordance with an exemplary embodiment of the present disclosure.

FIG. 15 illustrates a chemical extraction apparatus in accordance with an exemplary embodiment of the present disclosure.

FIG. 16 illustrates a top view of the chemical extraction apparatus depicted by FIG. 15.

FIG. 17 illustrates a side view of the chemical extraction apparatus depicted by FIG. 15.

FIG. 18 illustrates a cross-sectional view of the chemical extraction apparatus depicted by FIG. 17.

DETAILED DESCRIPTION

Figure 1:
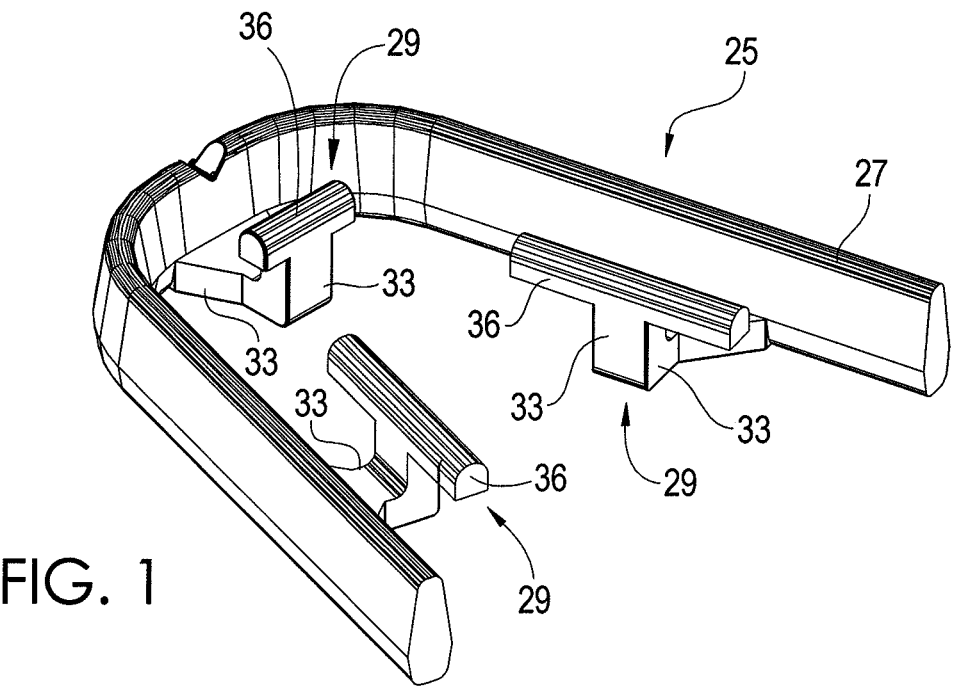
FIG. 1 illustrates a chemical extraction apparatus in accordance with an exemplary embodiment of the present disclosure.

The present disclosure generally pertains to apparatuses and methods for extracting volatile, semi-volatile, and non-volatile chemicals from a bodily cavity and breath. An apparatus for extracting chemicals in one exemplary embodiment is portable, convenient, and designed to easily fit in the bodily cavity. It is composed of absorbent material that is intended to remain in the bodily cavity for a period ranging from minutes to hours, although other time periods are possible. With each exhalation, air flows over the absorbents, and quantities of chemicals present in the breath are absorbed and/or adsorbed. As many (e.g., thousands) of breaths flow over the absorbent material, chemicals present in the breath are retained. Even trace levels of volatile chemicals present in the breath are sufficiently concentrated in the absorbent material over time to enable detection of these small amounts of chemicals via known analytical techniques. After a period of time, the apparatus is removed from the bodily cavity, and the absorbent material is analyzed by appropriate analytical instrumentation to determine the chemical compounds absorbed from the breath and bodily cavity (e.g., saliva).

Various types of materials may be used to absorb and/or adsorb chemicals from the breath and bodily cavity. Such materials include, but are not limited to, polydimethylsiloxane (PDMS), polyvinyl acetate, polyisoprene, styrene-butadiene rubber (SBR), polybutylene, polyacrylate, as well as other polymers that are known in the art, or may become known in the art, that are safe for use in bodily cavities. Such materials may be used in different ratios in combination with one another or alone by themselves. Softening agents such as microcrystalline wax may also be utilized to provide a softer, easy to mold polymer. Additional absorbent materials that may be incorporated into the device described herein include all forms of activated carbon with engineered pore sizes such as CarboPack or Carboxen materials, structures known as zeolites, an absorbent material called Tenax, and cyclodextrins.

Note that PDMS alone may be used as the absorbent material. One characteristic of PDMS is that it is hydrophobic. It does not bind water appreciably, but it does extract other volatile components present in a sample matrix (immersed in a liquid or from headspace) by absorption into the polymer liquid phase, making it ideal for use in the oral or nasal cavity environment.

Some absorbent material, such as activated carbon, may be hydrophilic. If such material is exposed to saliva for prolonged periods of time, the material may absorb significant quantities of water from the saliva thereby inhibiting the material's ability to absorb other compounds. In such embodiments, the material's contact with saliva may be limited. For example, as will be described in more detail hereafter, the absorbent material is positioned in a protection element that helps to reduce the material's contact with saliva. However, the protection element has at least one opening that allows breath to enter the protection element and contact the absorbent material. The use of the protection element helps to enhance the absorbent material's ability to absorb and/or adsorb compounds in the breath.

Moreover, regardless of which type of absorbent material is used, the absorbent extracts and retains volatile, semi-volatile, and non-volatile components from the breath and bodily cavity by absorption and adsorption. Forces and mechanisms responsible for the absorption and/or adsorption include Van der Waals forces, polarity, and hydrophobicity or hydrophillicity.

After absorption and/or adsorption, chemical components may be desorbed, analyzed, and measured by any of various types of analytical procedures and instruments. Such methods include, but are not limited to, thermal desorption and chemical desorption by exposure to solvent as with high performance liquid chromatography (HPLC). For thermal desorption, the absorbent is placed in a thermal desorption unit or heated chamber, equipped with inert gas flushing and temperature control. Upon heating the chamber, volatiles desorb from the absorbent material, are swept by inert gas (e.g., helium, nitrogen, argon) into a trap mechanism (e.g., a liquid nitrogen cooled cryo-trap, an absorbent material, or a combination thereof). The trap mechanism may be rapidly heated to release components and deposit them as a tight band on a capillary column for separation by a gas chromatograph (GC) and detection and measurement by a detector (e.g., mass spectrometer (MS), flame ionization, or flame photometric). Alternatively, the volatiles may be desorbed by solvent and analyzed by GC as previously described, or by HPLC. HPLC may utilize various detectors, such as MS, infra-red, ultraviolet, diode array, and/or other wavelength of electromagnetic radiation.

Data from the analysis may be used in a variety of ways. As an example, it may be determined that the presence of certain chemicals in certain quantities and/or a pattern of certain chemicals over time within the bodily cavity and/or breath may indicate the presence of a certain disease or condition. Thus, the data may be analyzed to predict or diagnose whether a user, which could be a human or an animal, has or will have a certain disease or condition. By keeping the absorbent in the bodily cavity for an extended period (e.g., several minutes or hours), even trace levels of chemicals can be concentrated in the absorbent allowing detection of such trace levels by conventional analytical equipment.

In one application, the absorbed chemicals are analyzed to determine whether the user has been exposed to (e.g., inhaled or otherwise consumed) certain chemicals. As a mere example, samples from a soldier may be analyzed to determine whether the soldier has been exposed to chemical weapons and, if so, to identify the type of chemicals to which he or she has been exposed. Various other types of conditions may be detected in other applications.

Figure 2:
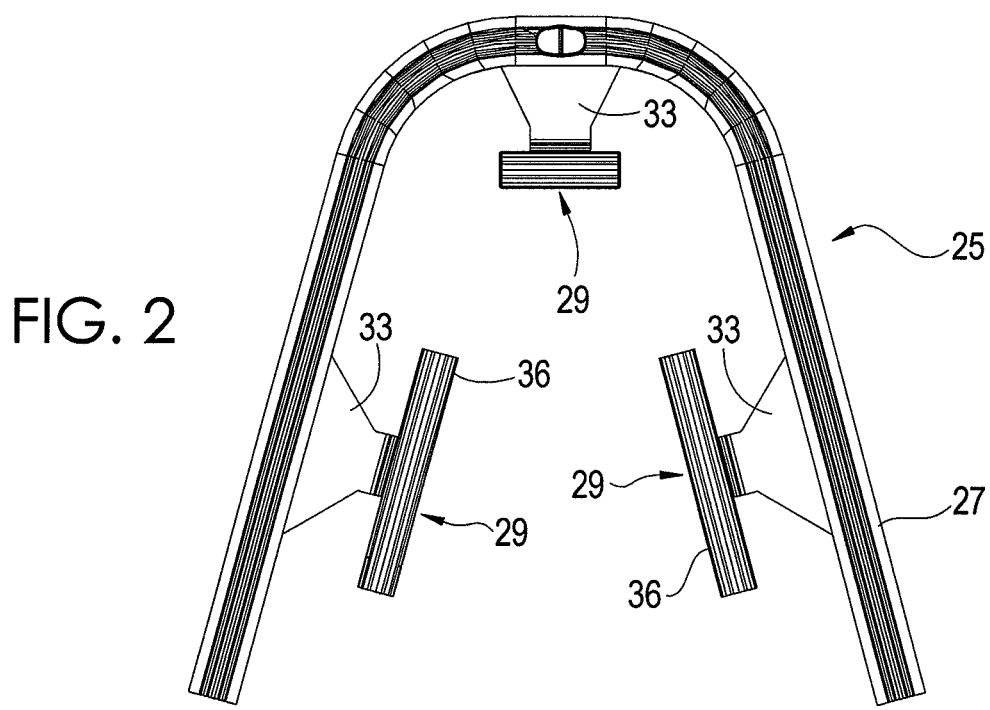
FIG. 2 illustrates a top view of the chemical extraction apparatus depicted by FIG. 1.
Figure 3:
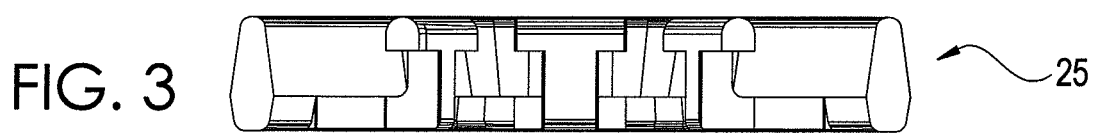
FIG. 3 illustrates a back view of the chemical extraction apparatus depicted by FIG. 1.

FIGS. 1-3 depict a chemical extraction apparatus 25 in accordance with an exemplary embodiment of the present disclosure. The apparatus 25 comprises a curved support element 27 that helps to support and appropriately position other components of the apparatus 25, as will be seen. The support element 27 has a shape corresponding with the expected shape of the teeth of a user who is to wear the apparatus 25. In this regard, the support element 27 is shaped such that it can be positioned along an outer side of the user's upper teeth. Thus, the support element 27 fits between the user's upper teeth and his or her upper lip. In other embodiments, the support element 27 could be shaped to fit around the user's lower teeth. The support element 27 is sufficiently elastic such that it presses against the user's teeth helping to hold the apparatus 25 is place, and it is sufficiently elastic to deform in order to accommodate various teeth dimensions, which can vary slightly from user-to-user.

The apparatus 25 has at least one tab 29 coupled to the support element 27. Each tab 29 comprises an arm 33 and a sample element 36, which is composed of absorbent material, such as PDMS or other material for absorbing and/or adsorbing chemicals from the oral cavity and breath. In one exemplary embodiment, the sample element 36 is composed entirely of an absorbent material, but other configurations are possible. Indeed, it is possible for only a portion of the sample element 36 to be composed of an absorbent material. For example, the sample element 36 may be composed of a non-absorbent material and coated with an absorbent material.

Each arm 33 extends from the support element 27 beneath at least one tooth of the user. Further, each arm 33 is coupled to a sample element 36 such that the sample element 36 is at a desired position within the oral cavity to enhance its ability for chemical absorption when the apparatus 25 is being worn.

Figure 4:
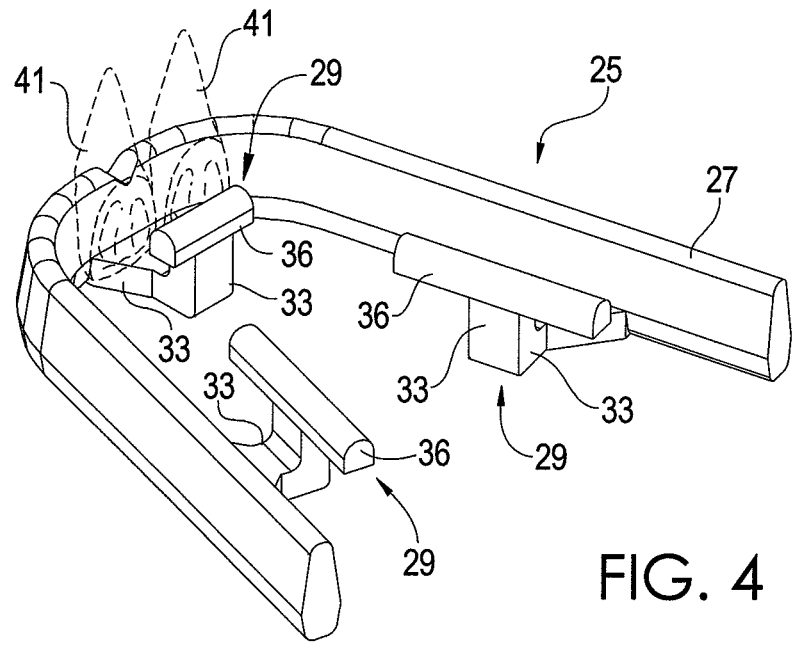
FIG. 4 illustrates an exemplary chemical extraction apparatus.
Figure 5:
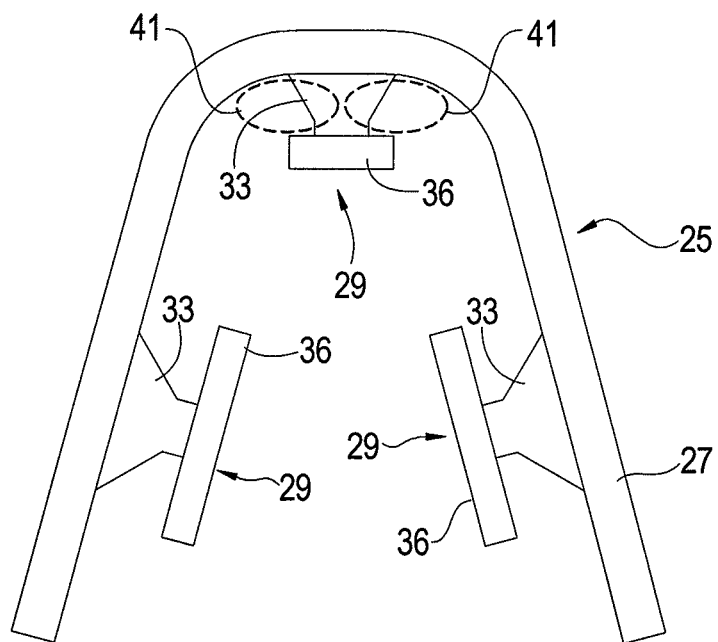
FIG. 5 illustrates the chemical extraction apparatus of FIG. 4 and the front two teeth of the user.

In one exemplary embodiment, each arm 33 is bent or otherwise curved such that the sample element 36 coupled to it contacts the back of the user's teeth. FIGS. 4 and 5 show one of the sampling elements 36 positioned behind a user's front teeth 41. The other teeth of the user are not shown for simplicity. However, for each sample element 36, at least one tooth is positioned between the sample element 36 and the support element 27. In one exemplary embodiment, the arm 33 is dimensioned such that the at least one tooth fits snugly between the sample element 36 and the support element 27 thereby helping to hold the apparatus 25 in place via frictional forces, thereby securing the apparatus 25 to the tooth. However, in other embodiments, the arm 33 for any sample element 36 may be dimensioned such that the sample elements 36 barely makes contact with at least one tooth or such that sample element 36 is separated from the user's teeth.

Figure 6:
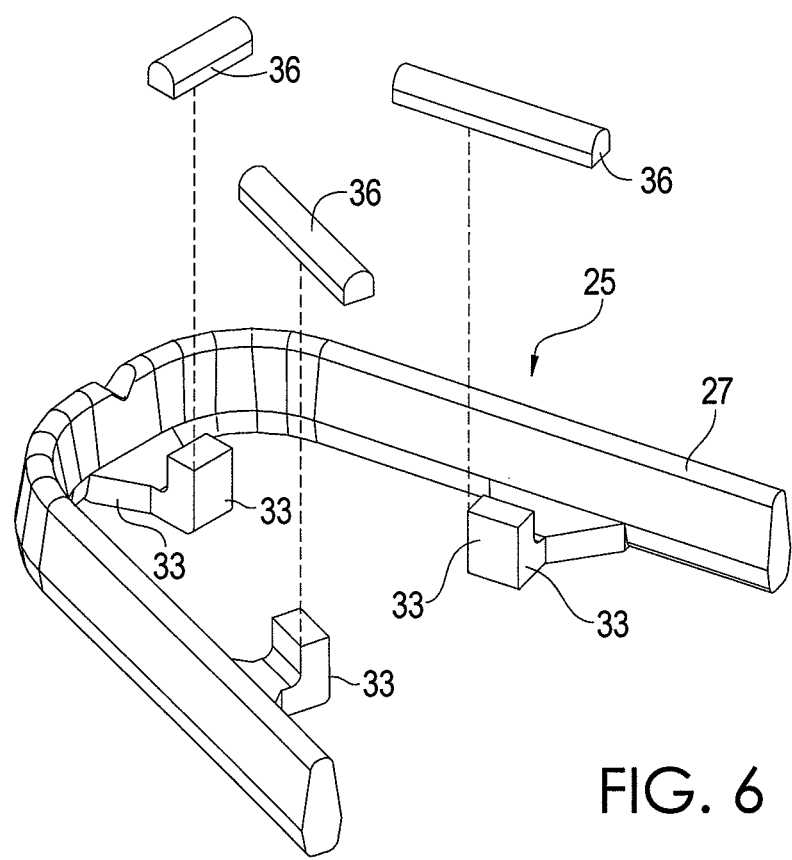
FIG. 6 illustrates the chemical extraction apparatus of FIG. 4 after sample elements have been removed from the apparatus.

While the apparatus 25 is being worn, each sample element 36 absorbs and/or adsorbs chemicals from the user's breath and oral cavity (e.g., saliva). After exposure for a desired duration, such as several minutes or hours, the apparatus 25 is removed from the oral cavity, and each arm 33 is cut by a razor or other sharp instrument to remove the sample elements 36, as shown by FIG. 6. The removed sample elements 36 can then be analyzed to determine the chemicals and the concentrations of the chemicals absorbed and/or adsorbed by the sample elements 36. The data from such analysis may then be used for a variety of purposes, such as diagnosing a disease or condition of the user (e.g., patient) or identifying a marker or predictor of a disease or condition.

In analytical chemistry, statistical validity is generally considered to be achieved after three analyses have been performed. Each of the three sample elements 36 can be separately analyzed in order to provide such statistical validity. However, it is possible for the apparatus 25 to have other numbers of sample elements 36 in other embodiments.

In one exemplary embodiment, the sample elements 36 are dimensioned according to the size requirements of the analytical equipment that is to be used for analyzing the sample elements 36. For example, many conventional thermal desorption units are designed to receive samples having a width of up to about 0.08 inches and a length of up to about 0.4 inches. To facilitate the use of the sample elements 36 with such equipment, each sample element 36 preferably has a width less than about 0.08 inches and a length less than about 0.4 inches. However, in other embodiments, other dimensions for the sample elements 36 are possible. Further, the sample elements 36 may be cut or otherwise arranged into any desired size or shape for analysis.

In addition, as described above, the sample elements 36 are composed of an absorbent material, such as PDMS. The other components of the apparatus 25 may be composed of the same or other materials. In one exemplary embodiment, the other components, such as the support element 27 and the arms 33, are composed of the same material as the sample elements 36. If the other components of the apparatus 25 are composed of an absorbent material, such as PDMS, then such other components may be analyzed as described above for the sample elements 36. If desired, such other components may be cut or otherwise arranged into any desired size or shape for analysis.

As shown by FIGS. 4 and 5, one of the sample elements 36 is positioned directly behind the upper front teeth 41 (referred to as "incisors") of the user. In fact, as described above, such sample element 36 may contact and possibly press against the inner side of the front teeth 41. Positioning absorbent material behind the front teeth 41 is generally ideal since breath typically flows across the upper palate of the user directly toward such location while the user is exhaling. Such a location may assist in the detection of trace levels of a chemical in the breath. The other sample elements 36 are positioned behind other teeth of the user, such as molars, bicuspids or canines.

Figure 7:
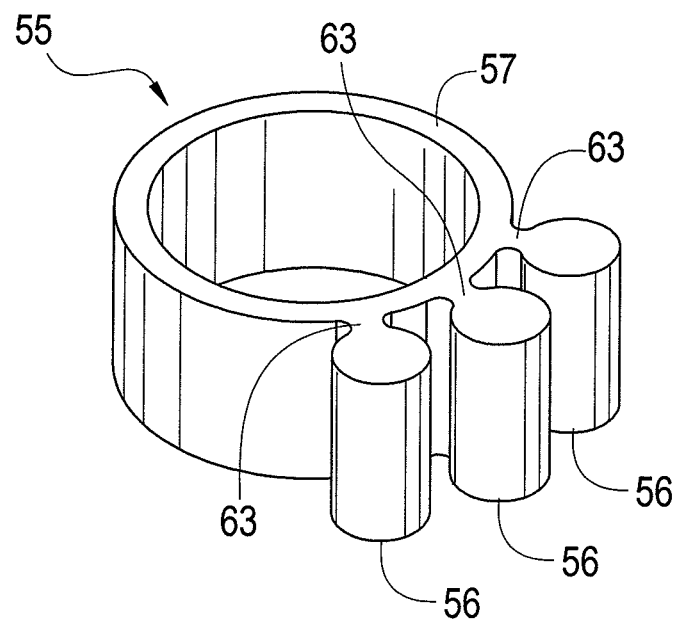
FIG. 7 illustrates a chemical extraction apparatus in accordance with an exemplary embodiment of the present disclosure.
Figure 8:
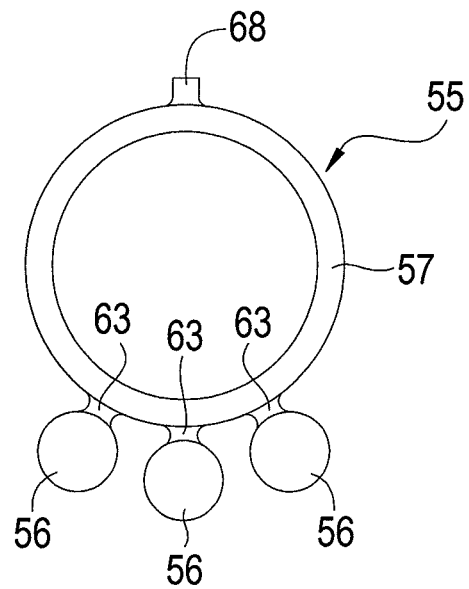
FIG. 8 illustrates a top view of the chemical extraction apparatus depicted by FIG. 7.

FIGS. 7 and 8 depict a chemical extraction apparatus 55 in accordance with an exemplary embodiment of the present disclosure. In the exemplary embodiment depicted by FIGS. 7 and 8, the apparatus 55 is configured such that multiple sample elements 56 can be positioned directly behind the front teeth 41.

In this regard, the apparatus 55 has a support element 57 that is coupled to three sample elements 56 by arms 63. In other embodiments, other numbers of sample elements 56 may be coupled to the support element 57. Each of the sample elements 56 is composed of an absorbent material, such as PDSM. In one exemplary embodiment, the sample elements 56 are composed entirely of an absorbent material, but other configurations are possible. Indeed, it is possible for only a portion of each sample element 56 to be composed of an absorbent material. For example, the sample elements 56 may be composed of a non-absorbent material and coated with an absorbent material.

As shown by FIGS. 7 and 8, the support element 57 is generally circular, but has sufficient elasticity such that it can deform and stretch. Further, the support element 57 is dimensioned such that it can be sufficiently stretched, like a rubber band, to extend around at least one tooth. In one exemplary embodiment, the support element 57 is dimensioned such that it can be sufficiently stretched to extend around the upper front two teeth 41 (referred to as "incisors") of the user. The inner diameter of the support element 57 is about 0.394 inches prior to stretching and deformation, and the outer diameter of the support element 57 is about 0.472 inches prior to stretching and deformation. Further, like the sample elements 36 of FIGS. 1-6, each of the sample elements 56 for the embodiment shown by FIGS. 7 and 8 has a length less than about 0.4 inches and a width less than about 0.08 inches in order to facilitate analysis of the sample elements 56 for some analytical equipment. Other dimensions for the support element 57 and the sample elements 56 are possible in other embodiments. Indeed, in other embodiments, the support element 57 can be dimensioned to fit around other numbers of teeth.

Figure 9:
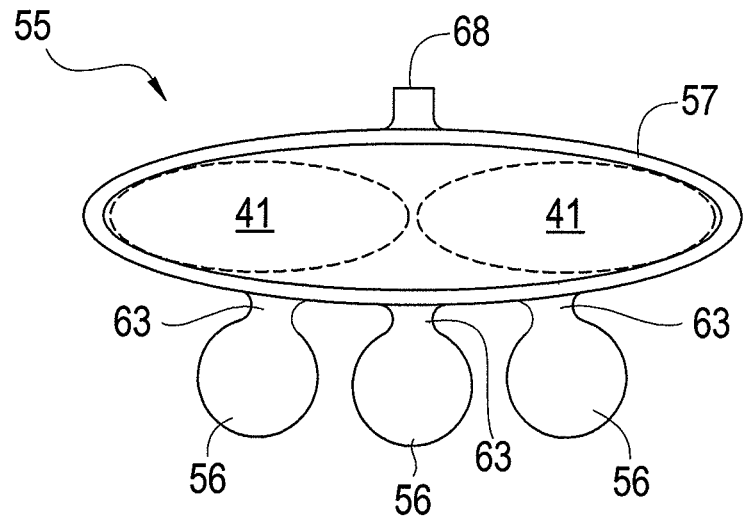
FIG. 9 illustrates the chemical extraction apparatus of FIG. 7 after the apparatus has been secured to the front teeth of a user.

In one exemplary embodiment, the support element 57 is positioned such that it snugly fits around the upper front two teeth 41, and the sample elements are positioned directly behind the front two teeth 41, as shown by FIG. 9. Thus, breath being exhaled should flow toward and contact the sample elements 56. The stretching of the support element 57 induces a frictional force that helps to hold the apparatus 55 in place while it is being worn as shown by FIG. 9.

After chemicals in the breath and oral cavity have been absorbed, the apparatus 55 can be removed by sliding the support element 57 down the tooth or teeth around which the support element 57 is wrapped until the support element 57 separates from the tooth or teeth. Using a razor or other sharp instrument, the arms 63 are cut to remove the sample elements 56 from the support element 57. The sample elements 56 can then be analyzed by analytical equipment, as described above for the sample elements 36.

Figure 10:
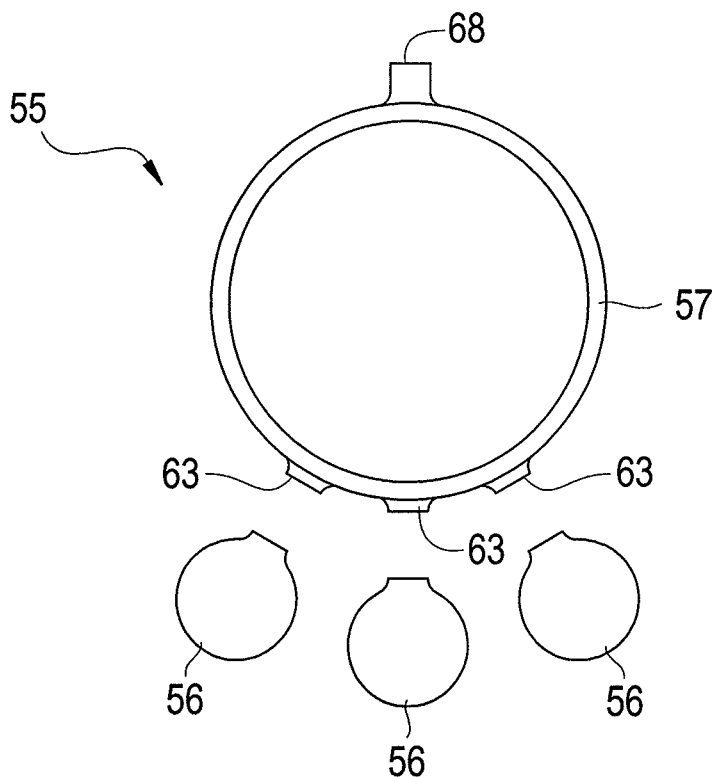
FIG. 10 illustrates the chemical extraction apparatus of FIG. 8 after sample elements have been removed from the apparatus.

As shown by FIGS. 8-10, the support element 57 has a tab 68 that can be grasped by a user to facilitate positioning and/or removal of the support element 57. In this regard, the tab 68 can be pinched between the fingers of the user or other person.

As described above, the sample elements 56 are composed of an absorbent material, such as PDMS. The other components of the apparatus 55 may be composed of the same or other materials. In one exemplary embodiment, the other components, such as the support element 57 and the arms 63, are composed of the same material as the sample elements 56. If the other components of the apparatus 55 are composed of an absorbent material, such as PDMS, then such other components may be analyzed as described above for the sample elements 56. If desired, such other components may be cut or otherwise arranged into any desired size or shape for analysis.

Figure 11:
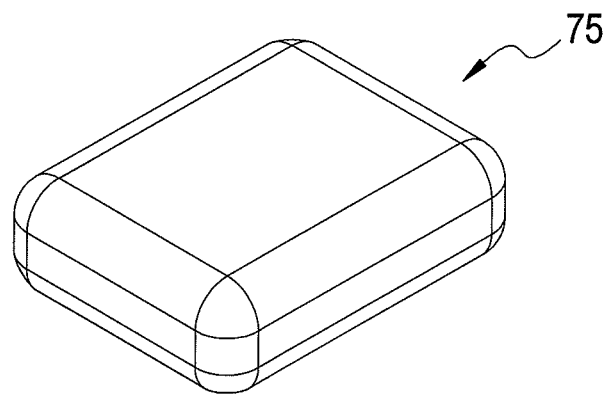
FIG. 11 illustrates a chemical extraction apparatus in accordance with an exemplary embodiment of the present disclosure.
Figure 12:
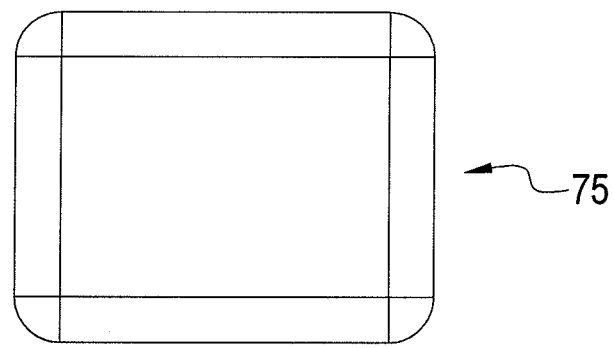
FIG. 12 illustrates a top view of the chemical extraction apparatus depicted by FIG. 11.
Figure 13:
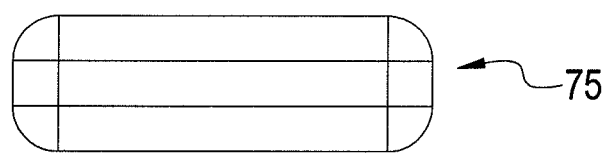
FIG. 13 illustrates a side view of the chemical extraction apparatus depicted by FIG. 11.

FIGS. 11-13 depict a chemical extraction apparatus 75 in accordance with an exemplary embodiment of the present disclosure. The apparatus 75 is composed of absorbent material. In addition, the apparatus 75 is chewable so that a user can place the apparatus 75 into his or her oral cavity and chew the apparatus, like gum. During chewing, the apparatus 75 is deformed, and saliva flow is stimulated. Chemicals present in saliva, oral cavity, and breath are extracted and absorbed into the absorbent material. After chewing for a desired time period sufficient to extract chemicals from the breath and saliva, the chewed apparatus 75 is then removed from the oral cavity and analyzed. If desired, the chewed apparatus 75 may be cut or otherwise re-shaped or arranged in an effort to facilitate analysis.

In one exemplary embodiment, the chewable apparatus 75 is composed of different combinations of heat resistant polymers, including polydimethylsiloxane (PDMS), polyvinyl acetate, polyisoprene, styrene-butadiene rubber (SBR), and polybutylene. Additionally a microcrystalline wax may be utilized as a softener. The apparatus 75 is designed to be chewed in a manner similar to chewing gum, and various known materials typically used in chewing gum may be used to manufacture the apparatus 75. Further, like other gum products, the apparatus 75 can have many different sizes and shapes, and the apparatus 75 can be manufactured using other known techniques for manufacturing chewing gum.

In one exemplary embodiment, PDMS is incorporated into the apparatus 75 by placing PDMS and other polymers into a mixer capable of providing sufficient shearing force such as a heated Z-blade mixer. In other embodiments, other types of absorbent material can be used. Contents are blended for a period (e.g., about 15 to 30 minutes) to provide a homogenous product and heated to temperatures that range from 50 degrees Celsius (C.) to 200 degrees C. Mixing is conducted until the formulations result in an apparatus 75 that is sufficiently malleable that it may be chewed by most healthy individuals. Formulations include concentrations of PDMS that range from 100% to 0%. Other polymers may be included in concentrations that range from 100% to 0%. Edible wax may be added to increase gum softness. Hydrophobic and hydrophilic nature of gum can be adjusted by selection and concentration of co-polymer utilized.

Other ingredients which may be added to the gum-like product of the present disclosure include other absorbents such as activated carbon, Carbopack, carboxen, edible wax for softening.

FIG. 14 depicts a chemical extraction apparatus 100 in accordance with an exemplary embodiment of the present disclosure. The apparatus 100 forms a pacifier that can be used by an infant or other user. The exemplary apparatus 100 of FIG. 14 has a sample element 102, a handle 103, and a support element 105. The handle 103 is in the shape of a ring, but other shapes of the handle 103 are possible in other embodiments. The handle 103 is coupled to the support element 105 and facilitates grasping of the apparatus 100 by a user. The sample element 102 is mounted on the support element 105 and forms a nipple to be inserted into the oral cavity of an infant or other user. The sample element 102 is composed of an absorbent material, such as PDMS. In one exemplary embodiment, the sample element 102 is composed entirely of an absorbent material, but other configurations are possible. Indeed, it is possible for only a portion of the sample element 102 to be composed of an absorbent material. For example, the sample element 102 may be composed of a non-absorbent material and coated with an absorbent material.

The sample element 102 is inserted through a user's mouth into the oral cavity of a user, similar to a nipple of a conventional pacifier. While in the oral cavity, the absorbent material of the sample element 102 absorbs and/or adsorbs chemicals from the breath and saliva of the user. After chemicals in the breath and oral cavity have been absorbed for a desired period, such as several minutes or hours, the apparatus 55 is removed from the user's oral cavity. Using a razor or other sharp instrument, the sample element 102 is cut to remove the sample element 102 or at least a portion of the sample element 102 from the support element 57. The removed sample element portion can then be analyzed by analytical equipment, as described above for the sample elements 36.

It should be noted that there are many different conventional pacifier configurations that can be used to implement the apparatus 100. The embodiment shown by FIG. 14 is exemplary.

FIGS. 15-17 depict an exemplary embodiment of a chemical extraction apparatus 125 in accordance with an exemplary embodiment of the present disclosure. The apparatus 125, like the apparatus 100 shown by FIG. 14, forms a pacifier. As shown by FIGS. 15-17, the apparatus 100 has a support element 127 that is coupled to a hollow protection element 133 via an arm 135. The protection element 133 is inserted into the oral cavity of an infant or other user. It is possible for the protection element 133 to be composed of absorbent material that can be later analyzed similar to the apparatus 100 shown by FIG. 14. However, other materials for the protection element 133 are possible.

As shown by FIG. 18, at least one sample element 149 is positioned within a cavity 145 of the protection element 133. In one exemplary embodiment, the apparatus 125 has three sample elements 149 to provide statistical validity, but other numbers of sample elements 149 are possible in other embodiments. Each sample element 149 is composed of an absorbent material that extracts chemicals from the user's breath. In one exemplary embodiment, each sample element 149 is composed entirely of an absorbent material, but other configurations are possible. Indeed, it is possible for only a portion of each sample element 149 to be composed of an absorbent material. For example, each sample element 149 may be composed of a non-absorbent material and coated with an absorbent material. In addition, each sample element 149 is dimensioned similar to the sample elements 36 described above for FIGS. 1-6. However, other dimensions of the sample elements 149 are possible in other embodiments.

In the embodiment shown by FIG. 18, each sample element 149 is coupled to an inner wall of the protection element 133 via a respective arm 152, which may be cut by a razor or other sharp instrument in order to separate the sample element 149 from the protection element 133. Other techniques for coupling the sample elements 149 to the protection element 133 and/or positioning the sample elements 149 within the cavity 145 are possible.

A hole 142 in the protection element 133 allows the user's breath to flow into the cavity 145 and contact the sample elements 149, which absorb or adsorb chemicals from the breath while protection element 133 is in the oral cavity. However, the protection element 133 helps to keep saliva from reaching the sample elements 149, although it is possible for some saliva to enter the cavity 145 via the hole 142. Limiting the amount of saliva that contacts the sample elements 149 may be particularly beneficial when the absorbent material of any of the sample elements 149 is hydrophilic. In this regard, limiting the exposure of hydrophilic absorbent material to saliva reduces the amount of water absorbed by such material thereby enhancing the material's ability to extract chemicals from the user's breath. Note that the hole 142 may be located at positions other than that shown by FIG. 15, and the protection element 133 may have any number of holes. The number and size of the holes can be selected depending on the degree to which contact of the absorbent material with saliva is to be limited.

The protection element 133 is inserted through a user's mouth into the oral cavity of a user, similar to a nipple of a conventional pacifier. While in the oral cavity, the absorbent material of each sample element 149 absorbs and/or adsorbs chemicals from the breath of the user. After chemicals in the breath have been absorbed for a desired period, such as several minutes or hours, the apparatus 125 is removed from the user's oral cavity. Using a razor or other sharp instrument, the protection element 149 to provide access to the sample elements 149, which are then removed from the cavity 145. In the embodiment shown by FIG. 18, the arms 152 are cut to remove the sample elements 149. However, it is possible for the sample elements 149 to reside in the cavity 145 without being coupled to the protection element 133. If desired, the sample elements 149 may be cut or otherwise rearranged for analysis. The absorbent material of the sample elements 149 can be analyzed by analytical equipment, as described above for the sample elements 36.

In various embodiments described above, absorbent material is positioned within the oral cavity of a user for a period of time. Volatile, semi-volatile, and non-volatile chemicals are extracted from the breath and saliva of the user. By keeping the absorbent material in the oral cavity for an extended period of time, such as several minutes or hours depending on the types of materials selected, even trace levels of a chemical can be concentrated in the absorbent material thereby enabling conventional analytical techniques to detect the chemical.

In one exemplary embodiment, absorbent material (e.g., PDMS) is positioned within a nasal cavity of a user or within the flow of breath from the nasal cavity to absorb and/or adsorb chemicals from the nasal cavity and/or breath flowing through the nasal cavity. There are various techniques that could be used to position absorbent material within a nasal cavity or the breath flowing through the nasal cavity. For example, the absorbent material may be coupled to a nostril attachment apparatus, such as a clamp, that can be detachably coupled to a nostril. At least one sample element composed of the absorbent material and dimensioned as described above for the sample elements 36 or otherwise may be coupled to the nostril attachment apparatus. Other configurations of the absorbent material are possible. After exposure within the nasal cavity or to the breath flowing through the nasal cavity, the sample element may be removed from the nostril attachment apparatus and analyzed, as described above, to determine the concentrations of chemicals absorbed and/or adsorbed by the sample element. Other techniques and/or types of devices may be used to position the absorbent material in or close to the nasal cavity.

Positioning the absorbent material to absorb and/or adsorb chemicals from the nasal cavity or breath flowing through the nasal cavity may have several advantages. For example, in embodiments in which a chemical extraction apparatus is positioned within an oral cavity, chemicals from the oral cavity, such as tooth or tongue plaque, might interfere to some extent with an analysis to determine the concentration of chemicals exhaled from the user's lungs. Positioning the absorbent material to absorb and/or adsorb chemicals from the nasal cavity or breath flowing through the nasal cavity would prevent interference by chemicals in the oral cavity.

Figure 19:
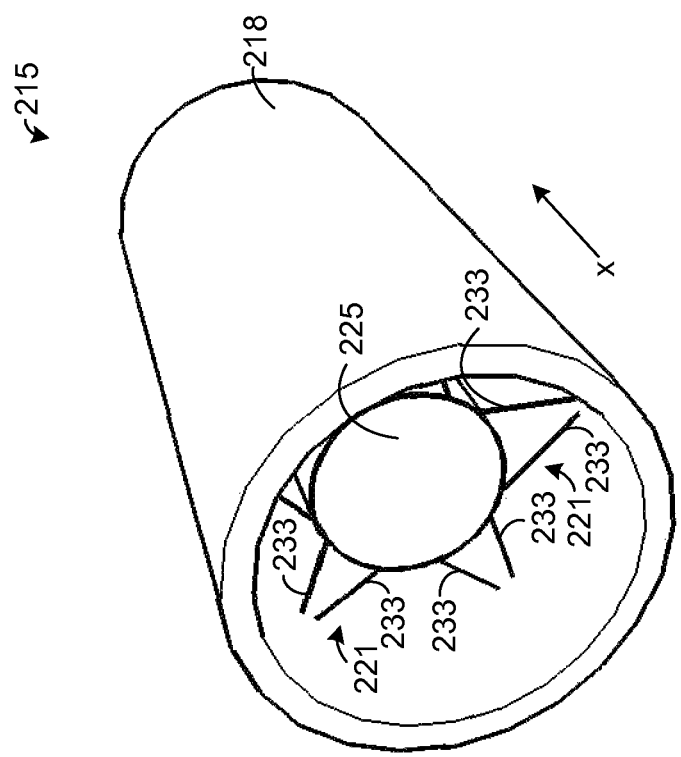
FIG. 19 illustrates an exemplary chemical extraction apparatus that is holding a sample element.

FIG. 19 depicts a chemical extraction apparatus 215 in accordance with an exemplary embodiment of the present disclosure. The apparatus 215 of FIG. 19 is adapted for insertion into a nasal cavity of a human, but the apparatus 215 may be adapted for insertion into nasal cavities of animals in other embodiments. As an example, the dimensions of the apparatus 215 may be specifically tailored for the size of the nostril into which the apparatus 215 is to be inserted.

The exemplary apparatus 215 of FIG. 19 comprises a hollow support element 218 that has a tubular shape. In one exemplary embodiment, the support element 218 forms a hollow cylinder with constant inner and outer diameters. As an example, the outer diameter is about 1 cm, and the wall thickness of the support element 218 (i.e., the distance from the element's inner surface to its outer surface) is about 1 millimeter (mm). Further, the length of the support element 218 in the x-direction is about 2 cm. In other embodiments, other dimensions are possible. In addition, in other embodiments, the support element 218 can be tapered such that its inner and outer diameters either decrease or increase along a length of the support element 218 in the x-direction.

Preferably, the support element 218 is dimensioned to fit snugly into a nostril of a user from which chemicals are to be extracted. The support element 218 may be inserted into the nostril by hand such that the entire length or a substantial portion of the length of the support element 218 is in the user's nostril. The snug fit of the apparatus 215 in the nostril holds the apparatus 215 in place while chemicals are absorbed, and the apparatus 215 may be pulled from the nostril by hand, such as by grasping and pulling the support element 218. Also, it is possible to apply pressure on an exterior of the nostril at the end of the support element 218 that is inserted the furthest into the nostril in order to force the apparatus 215 out of the nostril. While the apparatus 215 is inserted into the user's nostril, breath may flow through the interior region of the support element 218.

Figure 20:
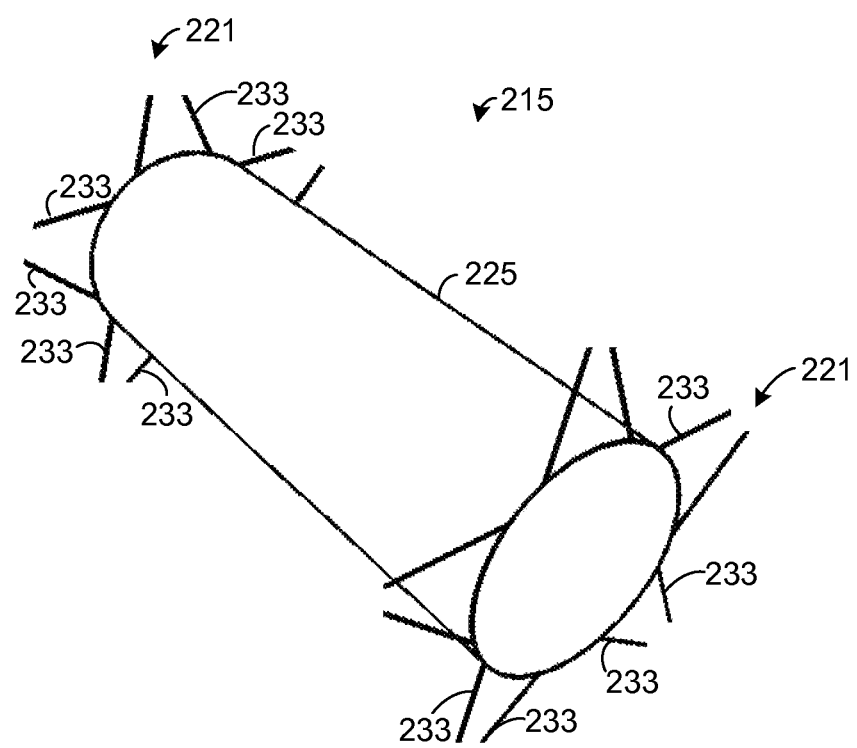
FIG. 20 illustrates a sample element and a pair of frames for holding the sample element in the chemical extraction apparatus depicted by FIG. 19.
Figure 21:
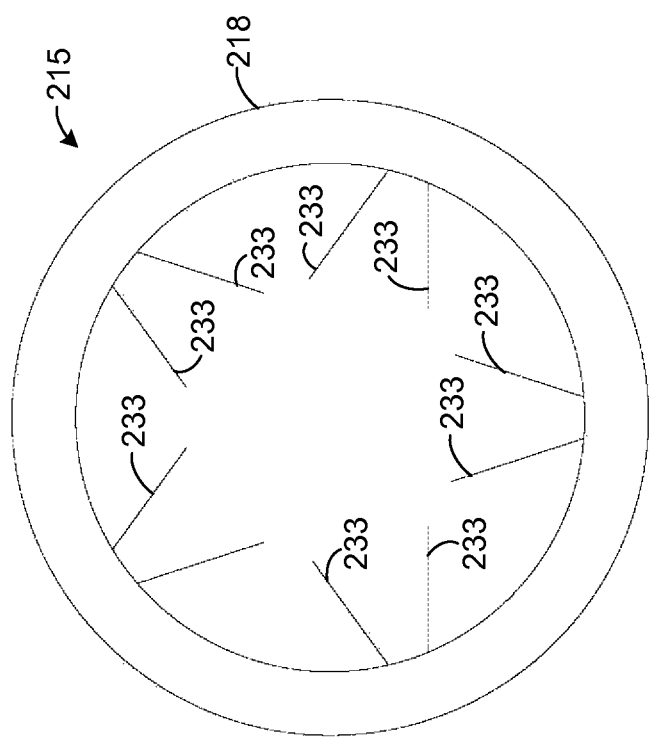
FIG. 21 illustrates an end view of the chemical extraction apparatus depicted by FIG. 19.

FIG. 20 shows the apparatus 215 with the support element 218 removed for illustrative purposes. Referring to FIGS. 19 and 20, the apparatus 215 comprises a plurality of frames 221 for holding at least one sample element 225. FIG. 21 depicts an end view of the apparatus 215 with the sample element 225 removed for illustrative purposes. In one exemplary embodiment, the sample element 225 is composed entirely of an absorbent material, such as PDMS, but other configurations of the sample element 225 are possible. In the exemplary embodiment shown by FIG. 20, the sample element 225 is in the shape of a solid cylinder, but other shapes are possible. In addition, as will be described below for other embodiments of the sample element 225, the sample element 225 may be hollow, allowing breath to flow through an inner region of the sample element 225.

Each frame 221 comprises a plurality of arms 233 that extend from an inner surface of the support element 218 to the sample element 225. The arms 233 hold the sample element 225 in place while breath flows through the frame 218 contacting the sample element 225. In the exemplary embodiment shown by FIGS. 19-21, there are ten arms 233 in each frame 221, but other numbers of the arms 233 are possible in other embodiments. In one exemplary embodiment, the length of each arm from the inner surface of the support element 218 to the sample element 225 is about 0.3 centimeters (cm). In the embodiment shown by FIGS. 19-21, each arm 233 forms a rod that is coupled to the sample element 225 at one end and to the inner surface of the support element 218 at the other end. Further, the region between any arm 233 and an adjacent arm 233 is hollow such that breath may flow between the arms 233. In this regard, the arms 233 form a wire frame 221 that allows breath to pass through the frame 221. In other embodiments, other dimensions and configurations of the arms 233 and other types of frames 221 are possible, and it is possible for each arm 233 to have any desired cross-sectional shape, such as circular, for example.

Further, it is possible for the support element 218 and arms 233 to be composed of any desired material. In one exemplary embodiment, the entire apparatus 25 is composed of an absorbent material, such as PDMS, but other materials suitable for insertion into a nasal cavity may be used provided that at least a portion is composed of absorbent material.

Figure 22:
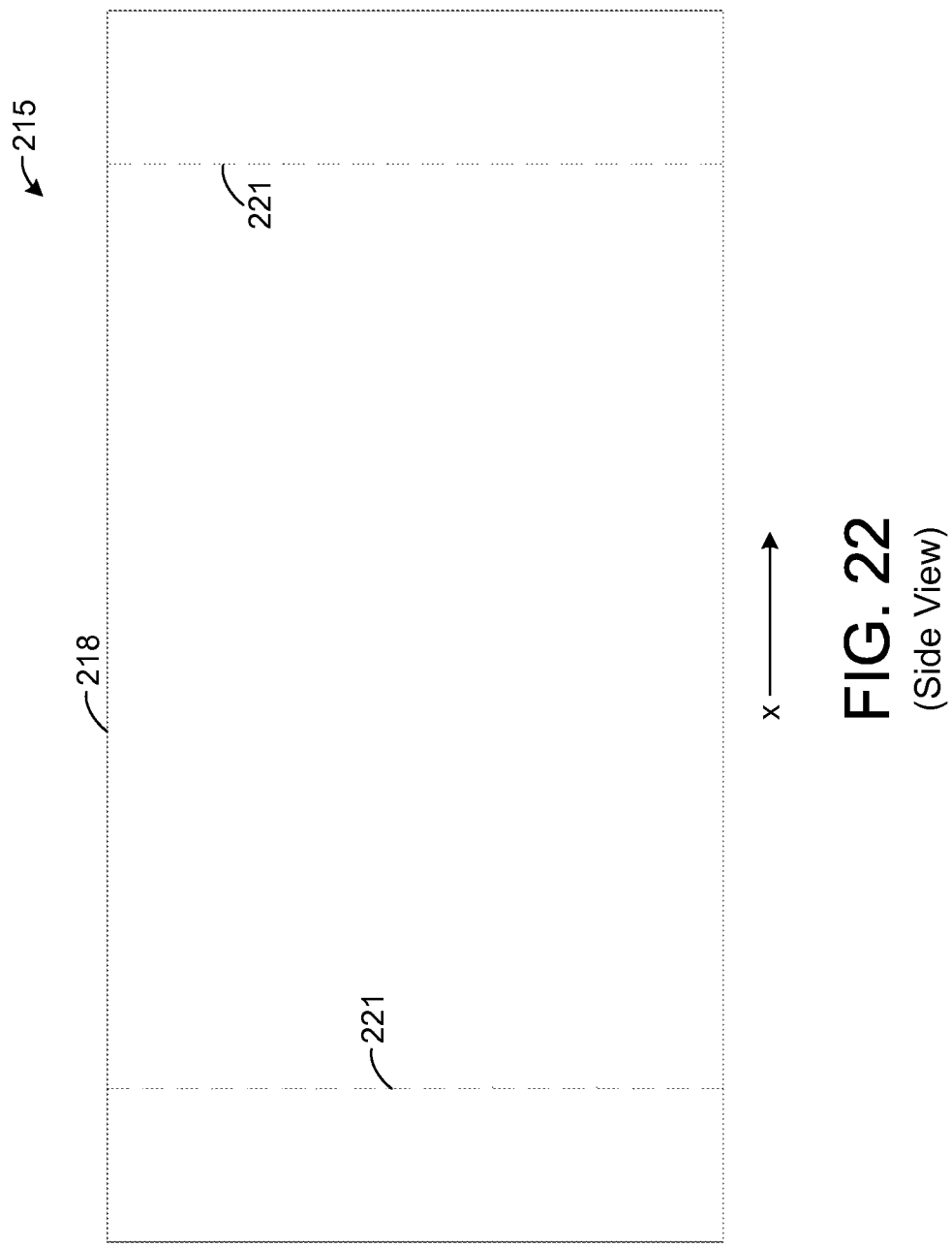
FIG. 22 illustrates a side view of the chemical extraction apparatus depicted by FIG. 19.

FIG. 22 shows a side view of the apparatus 215. The dotted lines 221 represent the approximate locations of the two frames 221. In other embodiments, other numbers of frames 221 are possible. In one exemplary embodiment, the length of the support element 218 in the x-direction is about 2 cm, and each frame 221 is positioned about 0.25 cm from a respective end of the support element 218. However, other dimensions are possible in other embodiments.

Figure 23:
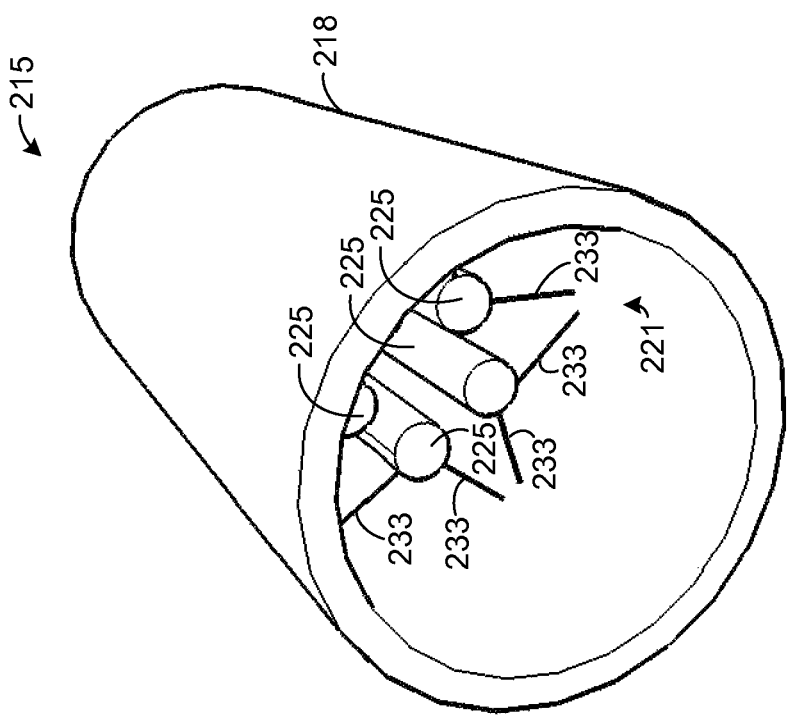
FIG. 23 illustrates an exemplary chemical extraction apparatus that is holding a plurality of sample elements.
Figure 24:
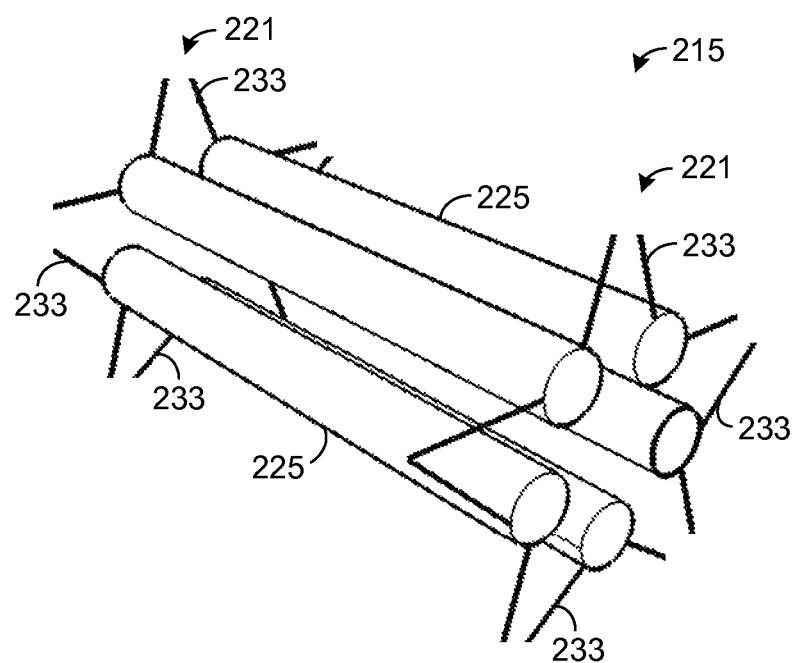
FIG. 24 illustrates a sample element and a pair of frames for holding the sample element in the chemical extraction apparatus depicted by FIG. 23.

FIG. 23 shows an exemplary embodiment of the apparatus 215 in which a plurality of sample elements 225 are held by the apparatus 215 instead of a single, larger sample element 225, as is shown by FIG. 19. FIG. 24 shows the apparatus 215 of FIG. 23 with the support element 218 removed for illustrative purposes. For each frame 221, a given sample element 225 is coupled to a pair of the frame's arms 233. Thus, each sample element 225 is coupled to a total of four arms 233 (two arms from each frame 221). Accordingly, in an embodiment in which each frame 221 has ten arms 233, as shown, five sample elements 225 are mounted to the support element 218. In the exemplary embodiment shown by FIG. 23, each of the sample elements 225 is solid and forms a non-tapered, cylindrical shape, but other types of sample elements 225 and sample element shapes are possible. As an example, hollow sample elements 225 may be used, as will be described in more detail below. Further, the sample elements 225 may be tapered, if desired.

Figure 25:
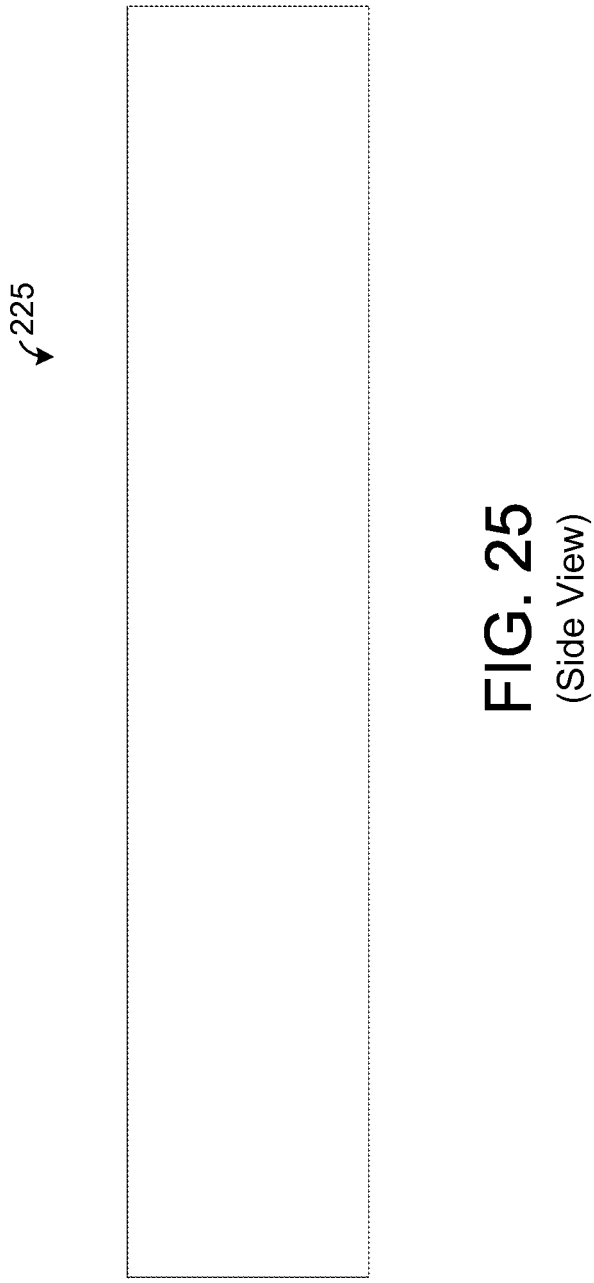
FIG. 25 illustrates a side view of an exemplary sample element.
Figure 26:
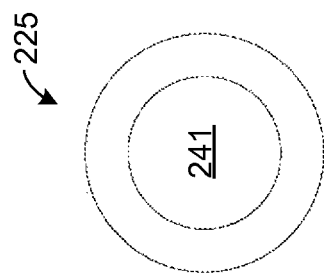
FIG. 26 illustrates an end view of the sample element depicted by FIG. 25.

FIGS. 25 and 26 depict an exemplary embodiment of a sample element 225 that is hollow and forms a tubular shape. In such an embodiment, breath may flow through a hollow inner region 241, and chemicals from such breath may be absorbed via the inner surface of the sample element 225. Such an embodiment, generally helps to increase the overall surface area that is exposed to the user's breath relative to an embodiment without a hollow region 241. In one exemplary embodiment, the outer diameter of the sample element 225 is about 0.25 mm with a wall thickness of about 0.1 mm leaving an inner diameter (i.e., diameter of the hollow region 241) of about 0.05 mm. Further, a length of the sample element 225 is about 1.5 cm allowing the sample element 225 to extend between the two frames 221 in the exemplary embodiment described above in which the frames 221 are about 1.5 cm apart. Other dimensions of the sample element 225 are possible in other embodiments.

However, note that keeping the length of the sample element 225 to about 2 cm or less and the width of the sample element 225 to about one-eighth (⅛) of an inch or less may have certain advantages. In particular, many standard analytical instruments, such as gas chromatograph, are configured to accept samples having a maximum length of about 2 cm and a maximum width of about one-eighth (⅛) of an inch. Keeping the dimensions of the individual sample elements 225 within such size requirements enables the sample elements 225 to be removed and inserted into such conventional equipment without having to modify (e.g., cut) the sample elements 225 thereby facilitating the chemical analysis process.

Figure 27:
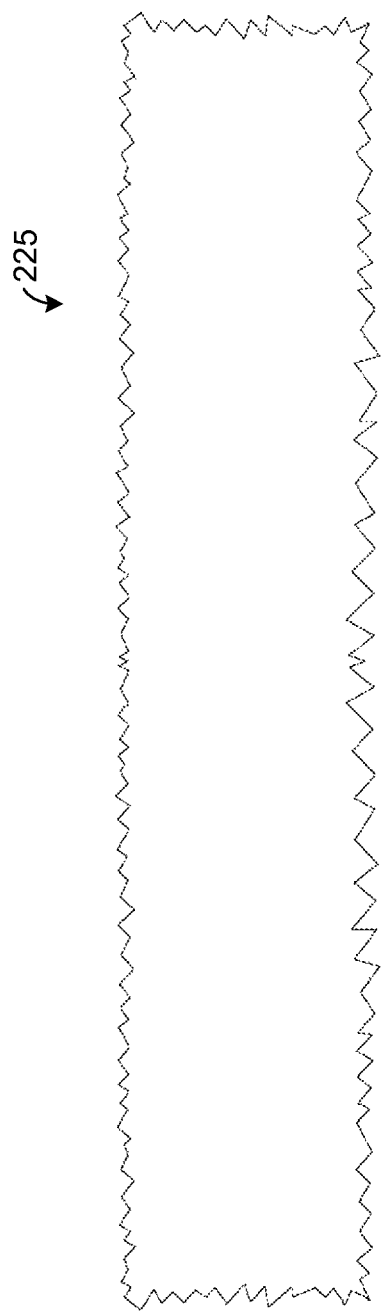
FIG. 27 illustrates a side view of an exemplary sample element having a fractile geometric shape.
Figure 28:
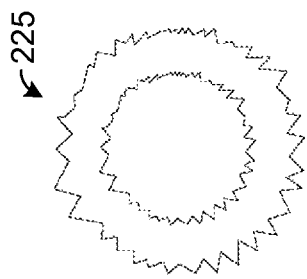
FIG. 28 illustrates an end view of the sample element depicted by FIG. 27.

In the exemplary embodiment shown by FIGS. 25 and 26, the inner and outer surfaces of the sample element 225 are generally smooth. FIGS. 27 and 28 show an exemplary embodiment of a sample element 225 having inner and outer surfaces that are not smooth. In this regard, the surfaces exhibit a fractal geometric shape such that the surfaces are rough or jagged. Such a shape generally increases the surface area of the absorbent material for a given set of element dimensions. For example, in one exemplary embodiment, the dimensions of the sample element 225 shown by FIGS. 27 and 28 are the same as those described above for the sample element 225 of FIGS. 25 and 26. However, the surface area of absorbent material is greater for the embodiment shown by FIGS. 27 and 28 due to the fractal geometric shape of the inner and outer surfaces.

Figure 29:
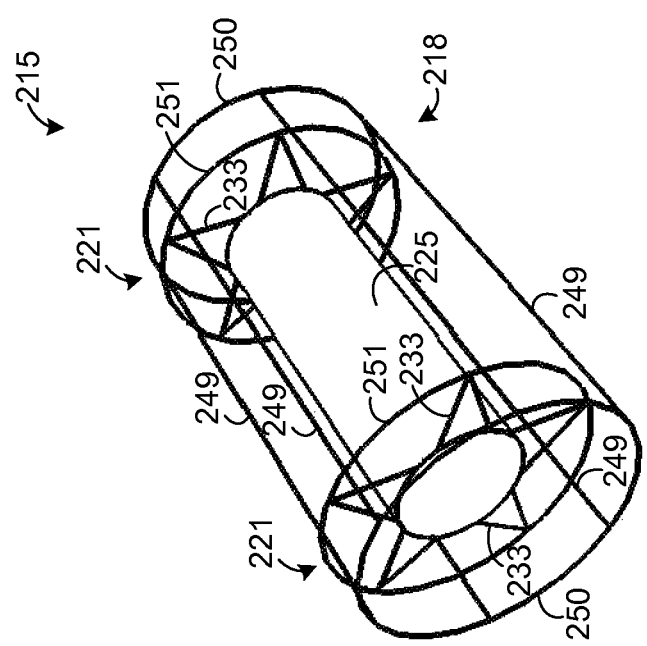
FIG. 29 illustrates an exemplary chemical extraction apparatus that is holding a sample element.
Figure 30:
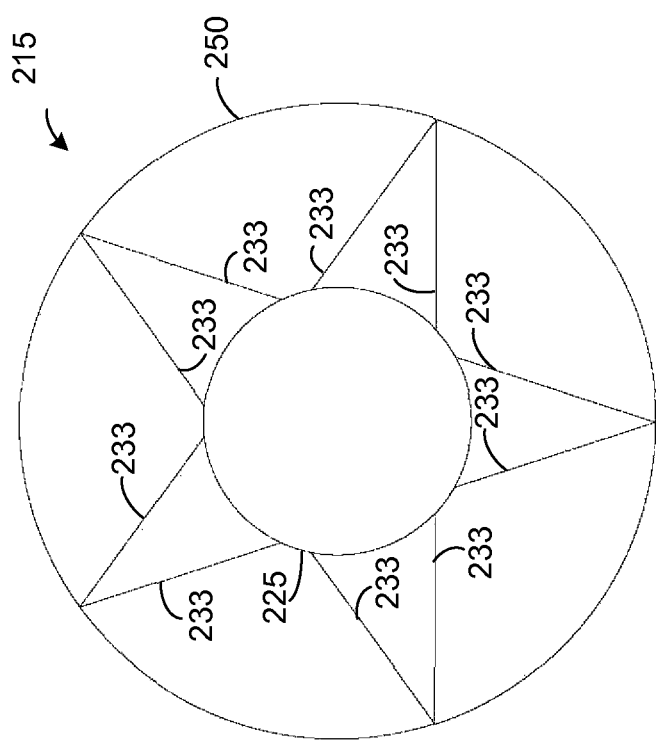
FIG. 30 illustrates an end view of the chemical extraction apparatus depicted by FIG. 29.

In the embodiment depicted by FIGS. 19-21, the wall of the support element 215 is shown to be solid. However, other types of support elements 215 are possible. As an example, FIG. 29 depicts an exemplary embodiment in which the support element 218 comprises a plurality of interconnected rods 249-251 such that the support element 218 forms a wire frame for holding other components of the apparatus 215. FIG. 30 shows an end view of the apparatus 215 depicted by FIG. 29.

As shown by FIGS. 29 and 30, the support element 218 has a plurality of circular rods 250 that form ends of the support element 218 and that are coupled to a plurality of straight rods 249. Each of the straight rods 249 extends from one of the circular rods 250 to the other circular rod 250. Further, there is a pair of circular rods 251, one for each frame 221. Each circular rod 251 is coupled to each of the rods 249 and to each arm 233 of a respective one of the frames 221. Each circular rod 251 provides additional mechanical stability at the point of contact for the arms 233 of a respective one of the frames 221. If desired, other circular rods (not shown) or other types of devices may be coupled to the support element 218 to provide additional mechanical support.

Figure 31:
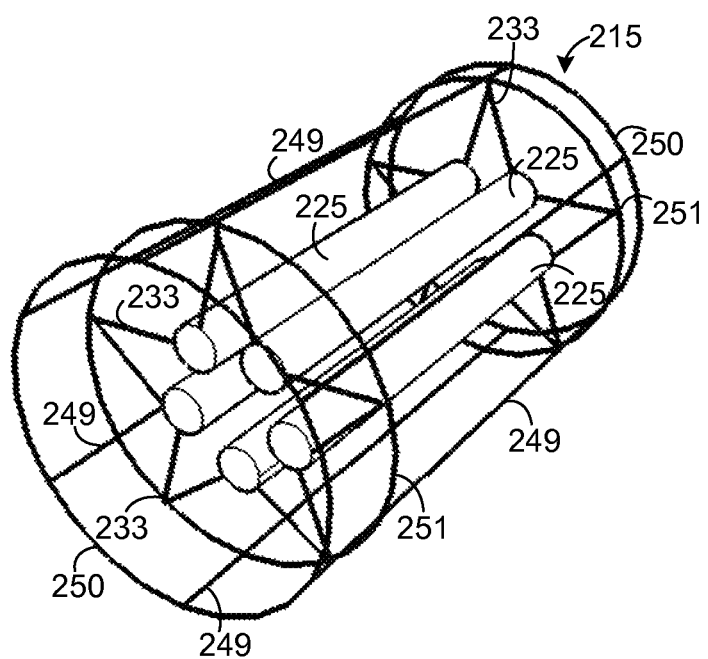
FIG. 31 illustrates an exemplary chemical extraction apparatus that is holding a plurality of sample elements.
Figure 32:
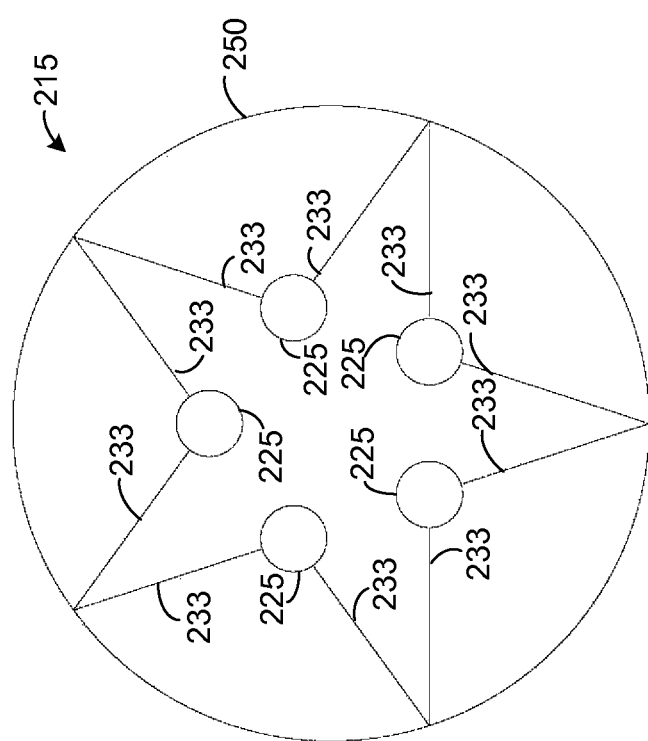
FIG. 32 illustrates an end view of the chemical extraction apparatus depicted by FIG. 31.

FIG. 31 depicts the support element 218 shown by FIG. 29 when a plurality of sample elements 225 are mounted to the support element 218, similar to the sample elements 225 mounted to the support element 218 depicted by FIG. 23. In this regard, as in the embodiment depicted by FIG. 23, each support element 225 is coupled to a total of four arms 233 but may be coupled to any number of arms 233 in other embodiments. FIG. 32 depicts an end view of the apparatus 215 depicted by FIG. 31.

Figure 33:
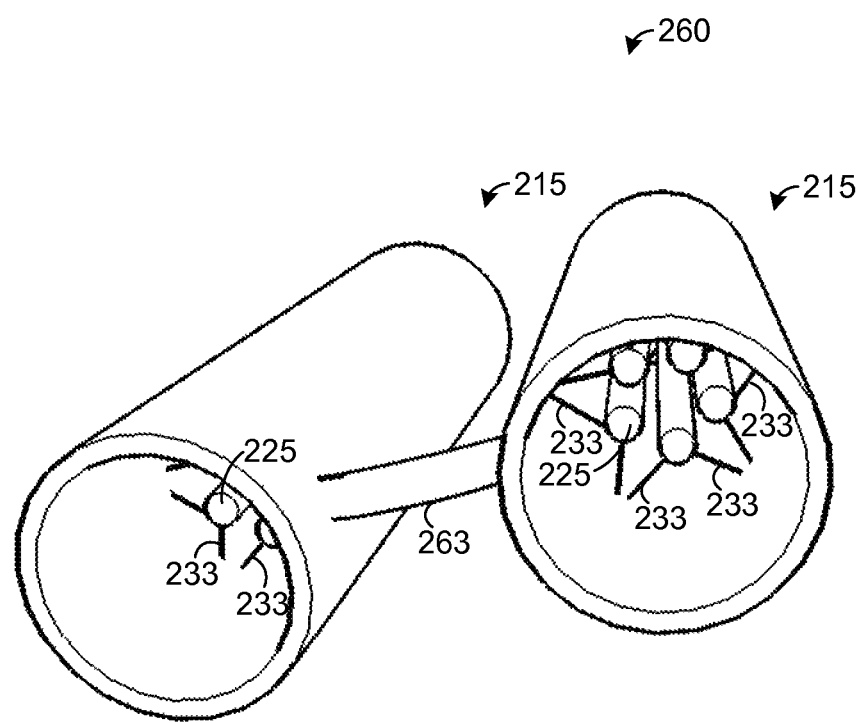
FIG. 33 illustrates an exemplary chemical extraction system.

FIG. 33 depicts an exemplary embodiment of a chemical extraction system 260 having a pair of chemical extraction apparatuses 215 depicted by FIG. 23. If desired, the chemical extraction apparatuses 215 may be replaced with any of the embodiments for a chemical extraction apparatus 215 described above. As shown by FIG. 33, the chemical extraction apparatuses 215 are coupled to one another via an arm 263 that extends from one of the chemical extraction apparatuses 215 to the other. During use, the system 260 may be positioned such that each chemical extraction apparatus 215 is inserted into a respective nostril of a user. Thus, one chemical extraction apparatus 215 absorbs chemicals from breath passing through one nostril, and the other chemical extraction apparatus 215 concurrently absorbs chemicals from breath passing through the user's other nostril. The apparatuses 215 may be pushed into the user's nostrils until the arm 263 contacts the bridge of the user's nose between his or her two nostrils. As in the embodiments of chemical extraction apparatuses for insertion into the oral cavity, any of the embodiments of chemical extraction apparatuses 215 for insertion into the nasal cavity can be used to absorb chemicals from the user's breath. A single chemical extraction apparatus 215 may be inserted into one nostril, or two chemical extraction apparatuses 215 may be inserted into both nostrils. While a chemical extraction apparatus 215 is inserted into a user's nostril, the sample element 225 absorbs chemicals from the user's breath that is passing through such nostril. Preferably, the chemical extraction apparatus 215 is secured such that it remains in the path of breaths from the user for many (e.g., thousands) breaths.

After chemicals in the breath and nasal cavity have been absorbed or adsorbed, the apparatus 215 is pulled from the nasal cavity. Using a razor or other sharp instrument, the arms 233 are cut to remove each sample element 225 from the other components of the apparatus 215. Each sample element 225 can then be analyzed via analytical equipment, as described above for the sample elements removed from the oral cavity. Based on such analysis, various conditions can be detected. As an example, a disease may be diagnosed based on the detection of certain chemicals at certain levels in a sample element 225. In another example, the analysis can reveal whether the user has inhaled or consumed certain chemicals as evidenced by the presence of certain chemicals at certain levels in a sample element 225. Various types of analysis may be performed on the sample elements 225 to detect various types of conditions of interest.

In one exemplary embodiment, the chemical measurements are displayed to a user via a display device (e.g., a monitor, liquid crystal display (LCD), printer) of a computer system. A computer system may be used to automatically analyze the measurements for predefined signatures of various diseases or conditions. If the measurements match such a predefined signature, information indicative of the match may be displayed. Yet other techniques for analyzing or utilizing the measurement are possible in other embodiments.

In any of the embodiments described above, flavor or scents can be added to the absorbent material or other portions of the chemical extraction apparatuses. When a chemical extraction apparatus is used in an oral cavity, flavor may be released into the user's oral cavity and tasted by the user. When a chemical extraction apparatus is used in a nasal cavity, at least one scent may be released into the user's nasal cavity and smelled by the user. The addition of flavor or scent may make the use of the chemical extraction apparatus more appealing to the user and/or increase the likelihood that the user will utilize the chemical extraction apparatus for the desired time.

In one exemplary embodiment, absorbent material is included in bones, toys, bridles, or other types of devices typically chewed by animals or otherwise positioned within the oral cavity of animals. For example, a bone to be chewed by a dog may include an absorbent material to absorb and/or adsorb chemicals from the dog's breath during chewing. The absorbent material can be removed after chewing for analysis to determine the concentrations of chemicals extracted from the dog's oral cavity and/or breath. In another example, absorbent material may be included in a portion of a bridle that is inserted into the oral cavity of a horse or other animal. Various other uses of the absorbent material are possible in other embodiments. If desired, the chewable device, such as a chewable toy, may be composed entirely of absorbent material, though it is possible for lone a portion of the chewable device to be composed of absorbent material.

In several embodiments described above, absorbent material is inserted into the oral or nasal cavity of a user. However, such insertion is unnecessary. For example, the absorbent material may be positioned outside of a bodily cavity but within the path of breath being exhaled by the user. As a mere example, a system similar to the one shown by FIG. 33 may be secured to the bridge of a user's nose between his or her nostrils and yet position absorbent material in a portion of the support element 218 outside of the nasal cavity but within the flow of breath from the user.

In one example, absorbent material, such as PDMS, is included in a respirator. As known in the art, a respirator is a device that is inserted into or covers the mouth and/or nose of a user. Some respirators have a filtering apparatus for filtering air being breathed by a user. Several such respirators are passive in that they do not force the user to inhale. Some respirators, such as respirators typically used in medical applications, force air or gas into the user and allow the user to exhale periodically. Such a respirator may be used for a user who is unable to breathe normally. There are many different types of conventional respirators that may be modified to include absorbent material, as described herein. Several respirators are described in the following U.S. patents, which are all incorporated herein by reference: U.S. Pat. Nos. 4,020,834; 4,227,519; 5,678,539; 5,423,313; 4,644,947; and 4,596,247.

In one exemplary embodiment, at least one sample element dimensioned like the sample elements 36 or 225 described above or otherwise is attached to a respirator such that breath from a user flows over the absorbent material, which absorbs and/or adsorbs chemicals from such breath. As an example, the respirator may have a tube that is inserted into the user's oral cavity, and the respirator may force air or other gas into the user's lungs through the tube. Further, air exhaled by the user may also pass through such tube. A sample element may be positioned within the tube or in-line with the air or other gas passing through the tube. In other embodiments, other configurations of the absorbent material may be used with a respirator to absorb and/or adsorb chemicals from a user's breath.

Now, therefore, the following is claimed:

1. A pacifier, comprising:
   a support element; and
   a nipple for insertion into an oral cavity of a user, the nipple coupled to the support element and having absorbent material for absorbing or adsorbing trace levels of volatile chemicals in breaths of the user, wherein the nipple has a cavity and the absorbent material is within the cavity of the nipple such that the absorbent material is positioned within the oral cavity when the nipple is inserted into the oral cavity, wherein the nipple has at least one hole for allowing the breaths to pass through the hole into the cavity of the nipple and contact the absorbent material, and wherein the at least one hole is dimensioned for limiting a flow of saliva into the cavity of the nipple, thereby increasing the trace levels of volatile chemicals absorbed or adsorbed from the breaths of the user.

2. The pacifier of claim 1, further comprising a handle coupled to the support element.

3. The pacifier of claim 1, wherein the absorbent material is hydrophilic.

4. The pacifier of claim 1, wherein an inner wall of the nipple within the cavity of the nipple comprises the absorbent material.

5. The pacifier of claim 1, wherein the absorbent material comprises polydimethylsiloxane (PDMS).

* * * * *